United States Patent
Constantine et al.

(10) Patent No.: US 8,697,037 B2
(45) Date of Patent: Apr. 15, 2014

(54) COMPOSITION

(75) Inventors: Mark Constantine, Poole (GB);
Margaret Joan Constantine, Poole (GB); Helen Elizabeth Ambrosen, Poole (GB)

(73) Assignee: Cosmetic Warriors Ltd, Dorset (GB)

( * ) Notice: Subject to any disclaimer, the term of this patent is extended or adjusted under 35 U.S.C. 154(b) by 0 days.

(21) Appl. No.: 13/202,400

(22) PCT Filed: Feb. 19, 2010

(86) PCT No.: PCT/GB2010/050293
§ 371 (c)(1),
(2), (4) Date: Oct. 20, 2011

(87) PCT Pub. No.: WO2010/094975
PCT Pub. Date: Aug. 26, 2010

(65) Prior Publication Data
US 2012/0034174 A1    Feb. 9, 2012

(30) Foreign Application Priority Data
Feb. 20, 2009    (GB) .................................. 0902937.2

(51) Int. Cl.
*A61K 8/46*    (2006.01)
*A61Q 11/00*    (2006.01)

(52) U.S. Cl.
USPC ............................................................. 424/56

(58) Field of Classification Search
USPC ............................................................. 424/56
See application file for complete search history.

(56) References Cited

U.S. PATENT DOCUMENTS 4,487,757 A * 12/1984 Kiozpeoplou .................. 424/49
6,811,793 B2 * 11/2004 Wehling ........................ 424/466

FOREIGN PATENT DOCUMENTS

| GB | 2 346 557 | 8/2000 |
|----|-----------|--------|
| GB | 2 346 619 | 8/2000 |
| WO | WO 93/14024 | 7/1993 |
| WO | WO 97/45103 | 12/1997 |
| WO | WO 00/47181 | 8/2000 |

OTHER PUBLICATIONS

Database WPI, Week 200917, Thomson Scientific, London, GB, AN 2009-B47418, XP002606686 & JP 2009 007303 A (KAO Corp), Jan. 15, 2009 * abstract.

* cited by examiner

*Primary Examiner* — Benjamin Packard
(74) *Attorney, Agent, or Firm* — Fay Sharpe LLP

(57) ABSTRACT

The present invention provides a surfactant product in the form of a solid comprising a surfactant, sodium carbonate and cream of tartar.

24 Claims, No Drawings

COMPOSITION

FIELD OF THE INVENTION

The present invention relates to a surfactant product, a process for producing said surfactant product, and a cosmetic method for using the surfactant product.

BACKGROUND TO THE INVENTION

The present invention relates to surfactants particularly those for use in contact with the human or animal body.

Surfactant products such as bubble baths, shampoos, shower gels and toothpastes are extremely well known cosmetic products and personal care products. These surfactant containing products are typically provided in the form of liquid or pastes. They are sold in containers to the end user and may be dispensed by the end user. However, the required use of packaging is a disadvantage. From an environmental perspective, waste packaging is a significant problem, despite the availability of recycling.

Some solid surfactant products have been provided. For example WO00/47181 discloses a surfactant product which is solid. This product is, for example, a bubble bath product in the form of a tablet or bar. When required for use, a portion of the solid product may be 'broken off' the bar and used. The products of WO00/47181 are formed from a composition containing cream of tartar, sodium bicarbonate and a surfactant. Although such bars have successfully provided a solution to the problem of packaging, they have certain disadvantages. We have found that cream of tartar and sodium bicarbonate react to liberate carbon dioxide. Thus during manufacture of the product an 'aerated' mixture is produced. This results in delays in the production process as time has to be allowed for the mixture to settle before the solid product can be moulded and formed. In addition, even after settlement, the moulded product contains a large number of pockets of entrapped gas. Thus the final solid product has a crumbly texture. Although this may be pleasant to use, it may result in the product disintegrating on use. This may prevent multiple use of a single dosage form, such as a bar, of the product.

The present invention seeks to provide surfactant products which do not require packaging, and yet allow for multiple use thereof.

SUMMARY OF THE INVENTION

In a first aspect, there is provided a surfactant product in the form of a solid comprising a surfactant, sodium carbonate and cream of tartar.

In a second aspect, there is provided a process for the production of a surfactant product comprising the steps of:
 i) preparing a mixture comprising a surfactant, sodium carbonate and cream of tartar.
 ii) allowing the mixture of step i) to solidify.

In a third aspect, there is provided a cosmetic method comprising contacting the moist skin of a user with the surfactant product of the present invention.

For ease of reference, these and further aspects of the present invention are now discussed under appropriate section headings. However, the teachings under each section are not necessarily limited to each particular section.

Advantages

We have found that in contrast to the prior art products containing sodium bicarbonate and cream of tartar, which in the presence of the water contained in the surfactant, create carbon dioxide gas, we may prepare a product in the form of a solid paste, which subsequently hardens in to a stable solid. The present solid products, for example a bubble bath bar which provides a bubble bath utilising its cream of tartar content, have a very different characteristics. The present products do not effervesce during production and provide a mixture during production which will harden. We have surprisingly found that the use of sodium carbonate, replacing in total or in part the sodium bicarbonate used in the previous solid products, results in a solid product, for example suitable for use in the bath, which is easier to manufacture, easier to use and had the added advantage of multiple use.

The use of sodium bicarbonate in bath products has long been known. The substitution of this well known product in this type of formulation gives very surprising and positive advantages. The paste, which becomes solid with some sodium carbonate replacing the sodium bicarbonate, does not become infused with carbon dioxide during production enabling the mixture to be shaped and cut efficiently.

The replacement of sodium bicarbonate with sodium carbonate results in a totally different type of product. The paste solidifies and hardens. The texture of the bar becomes solid and hard. When this product is introduced to running water, foam is generated to give the bath water the required effect. Surprisingly, the bar can be taken out of the water and left on the side of the bath where it will remain with a very hard texture until the next time it is used. The bath water can then again be run with the bar in the flow of water where it creates copious quantities of foam. Repeated use of the bar is facilitated as it retains its rock-like texture.

The replacement of sodium bicarbonate with sodium carbonate has created this innovation. Thus a re-usable bar (of solid bubble bath) which does not require a container, results.

The surfactant product of the present invention does not require additional packaging. Thus, the surfactant product of the present invention can be stored and used directly by the end user, without additional packaging. As a result, the environmental impact of waste packaging is greatly reduced.

The solid nature of the composition is further advantageous for users who are travelling with the product. Not only is the weight and volume of the product reduced, in scenarios where volume of liquid carried is restricted, such as during airline flights, the present product allows for the user to still carry the product.

DETAILED DESCRIPTION

Composition

As discussed herein, in one aspect of the present invention, there is provided a surfactant product in the form of a solid comprising a surfactant, sodium carbonate and cream of tartar.

Surfactant products of the present invention are compositions which can substantially sustain their physical shape when unsupported by external means, e.g. packaging etc. Thus, they are considered to be solid, solid like, in solid form or in solid-like form at room temperature.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

As mentioned above, due to the solid form of the compositions of the present invention, external packaging is not required to maintain the shape of the composition.

Surfactant

The surfactant product of the present invention comprises a surfactant. The surfactant is primarily selected from those surfactants known in the art to be suitable for application to the skin. In one embodiment, the surfactant is selected from the group consisting of sodium laureth sulfate, cocamide diethanolamine, lauryl betaine and mixtures thereof.

In one embodiment, the surfactant is a mixture of sodium laureth sulfate, cocamide diethanolamine and lauryl betaine.

In one embodiment, the surfactant is present in an amount of from about 10% to about 30% by weight of the total composition. Thus, where one surfactant is present, it may be present in an amount of from about 10% to about 30% by weight of the total composition. In a similar manner, where the surfactant is a mixture of one or more surfactants, the total amount of surfactant present is from about 10% to about 30% by weight of the total composition.

In one embodiment, the surfactant, or the mixture of surfactants, is present in an amount of from about 20% to about 30% by weight of the total composition.

In one embodiment, the surfactant, or the mixture of surfactants, is present in an amount of from about 22.5% to about 27.5% by weight of the total composition.

In one embodiment, the surfactant, or the mixture of surfactants, is present in an amount of about 25% by weight of the total composition.

The surfactant of the surfactant product provides the composition with the ability to achieve its required purpose. Thus for a bubble bath, the surfactant removes dirt and grease from the user's skin.

In one embodiment, the surfactant product is a bubble bath.
In one embodiment, the surfactant product is a shampoo.
In one embodiment, the surfactant product is a shower gel.
In one embodiment, the surfactant product is a toothpaste.
In one embodiment, the surfactant product is a facial wash.

Sodium Carbonate

The surfactant product of the present invention also comprises sodium carbonate. In one embodiment, sodium carbonate is present in an amount of from about 35% to about 60% by weight of the total composition.

In one embodiment, sodium carbonate is present in an amount of from about 35% to about 55% by weight of the total composition.

In one embodiment, sodium carbonate is present in an amount of from about 40% to about 50% by weight of the total composition.

In one embodiment, sodium carbonate is present in an amount of from about 42.5% to about 47.5% by weight of the total composition.

In one embodiment, sodium carbonate is present in an amount of about 45% by weight of the total composition.

Sodium carbonate ($Na_2CO_3$) is a sodium salt of carbonic acid. It is also known as washing soda or soda ash. It has many industrial, food and cosmetic uses.

Cream of Tartar

The surfactant product of the present invention also comprises cream of tartar. Cream of tartar is also known as potassium bitartrate or potassium hydrogen tartrate. It is the monopotassium salt of 2,3-dihydroxybutanedioic acid. Thus, the cream of tartar used in the surfactant product of the present invention encompasses any product which is considered to be cream of tartar by virtue of it substantially comprising potassium hydrogen tartrate.

In one embodiment, the cream of tartar of the surfactant product is potassium hydrogen tartrate.

In one embodiment, the cream of tartar is present in an amount of from about 20% to about 30% by weight of the total composition.

In one embodiment, the cream of tartar is present in an amount of from about 25% to about 30% by weight of the total composition.

In one embodiment, the cream of tartar is present in an amount of from about 27% to about 29% by weight of the total composition.

In one embodiment, the cream of tartar is present in an amount of about 28% by weight of the total composition.

Preferred Compositions & Additional Components

The surfactant product of the present invention may also comprise one or more cosmetically acceptable additives. The person skilled in the art is aware of a range of cosmetically acceptable additives which are suitable for incorporation into such compositions. Fruit and herb extracts and juices, vegetable oils and essential oils are all compatible with the composition. Colours, both naturally derived and synthetic can be used to colour the surfactant product.

In one embodiment, the cosmetically acceptable additives are selected from the group consisting of essential oils, vitamins, fragrances, colourings, decorative articles and mixtures thereof.

In one embodiment, the cosmetically acceptable additives are present in amount of from about 0.2% to about 3% by weight of the total composition.

The essential oils will be selected based on the fragrance desired, skin type to be treated and other effects desired based on the well known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the surfactant product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the surfactant product are selected from Tarragon, Lemon myrtle, Labdunum, and Lemon.

In one highly preferred embodiment, the solid product of the present invention is used in the method of British Patent Application No. 0822832.2 (the entire contents of which are incorporated herein by reference).

As discussed herein, vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin (s) may be provided from a synthetic source or from incorporation into the surfactant product of a material, such as a natural material, that has a high vitamin content.

The ingredients in the present invention do not require cosmetic preservatives, soublisers or alcohols, such as ethanol. The use of cosmetic preservatives can increase the potential to irritate the skin. The use of alcohols can cause the skin to become dry. Equally, fragrances do not need to be soublised and therefore soublisers can be avoided.

The decorative items which may be present in the surfactant product include items such as glitter, sequins, flowers, vegetables, parts thereof or mixtures thereof.

In a preferred embodiment, the surfactant product comprises a surfactant in an amount of about 25%, sodium carbonate in an amount of about 45%, and cream of tartar in an amount of about 28%.

The above ranges provide preferred amounts of each of the components. Each of these ranges may be taken alone or combined with one or more other component ranges to provide a preferred aspect of the invention.

Process

In another aspect, there is provided process for the production of a surfactant product comprising the steps of:

i) preparing a mixture comprising a surfactant, sodium carbonate and cream of tartar;

ii) allowing the mixture of step i) to solidify.

The shape of the surfactant products of the present invention is not limited. It may be that the surfactant products are provided with a shape which would be aesthetically pleasing and/or which aids in the application of the composition to the skin. For example, it may be that the surfactant product is produced in such a manner so that it solidifies in a shape which is ergonomically acceptable to the user.

Therefore, in one embodiment of the process of the present invention, the mixture of step i) is caused to solidify in a predetermined shape.

In one embodiment of the process of the present invention, the mixture of step i) is pressed into a mould, allowed to solidify, and then turned out to produce the surfactant product.

As described herein, the surfactant product may further comprise one or more cosmetically acceptable additives. In one embodiment, the process further comprises the step of combining with the mixture of step i) one or more cosmetically acceptable additives as defined above.

Method

In one aspect of the present invention, there is provided a cosmetic method comprising contacting the moist skin of a user with the surfactant product as defined herein.

The cosmetic method of the present invention can be applied to various areas of the skin, including the face, feet, torso or any other part of the body. In view of the solid nature of the product and the possible skin effects of sodium carbonate, the method preferably applies to 'hard' areas of skin such as that on feet.

As described herein, the moist skin of a user is massaged with the surfactant product of the present invention. Once the desired effect has been achieved, any excess of the composition can be removed by rinsing the applied area with water.

EXAMPLES

The invention will now be described with reference to the following non-limiting example.

A surfactant product having the following composition was prepared.

The formula is as follows:

|  | Wt % |
| --- | --- |
| Sodium Carbonate | 45% |
| Cream of Tartar | 28% |
| Surfactant | 25% |
| Fragrance | 2% |
|  | 100% |

According to the present invention the sodium carbonate and the cream of tartar are blended together thoroughly. The surfactant is then added, the mixture then forms a paste. This quickly solidifies and hardens. The texture becomes very hard and rock-like. This enables the resulting form to be introduced to running water where it does not disintegrate. It keeps its shape and texture allowing multiple uses of the same bar.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A surfactant product in the form of a solid comprising a surfactant, sodium carbonate and cream of tartar.

2. A surfactant product according to claim 1, comprising a surfactant in an amount of from about 10% to about 30% by weight of the total composition.

3. A surfactant product according to claim 2, comprising a surfactant in an amount of from about 20% to about 30% by weight of the total composition.

4. A surfactant product according to claim 3, comprising a surfactant in an amount of from about 22.5% to about 27.5% by weight of the total composition.

5. A surfactant product according to claim 1, wherein the surfactant is selected from the group consisting of sodium laureth sulfate, cocamide diethanolamine, lauryl betaine and mixtures thereof.

6. A surfactant product according to claim 1, comprising sodium carbonate in an amount of from about 35% to about 60% by weight of the total composition.

7. A surfactant product according to claim 6, comprising sodium carbonate in an amount of from about 40% to about 50% by weight of the total composition.

8. A surfactant product according to claim 1, comprising cream of tartar in an amount of from about 20% to about 30% by weight of the total composition.

9. A surfactant product according to claim 8, comprising cream of tartar in an amount of from about 25% to about 30% by weight of the total composition.

10. A surfactant product according to claim 9, comprising cream of tartar in an amount of from about 27% to about 29% by weight of the total composition.

11. A surfactant product according to claim 1, comprising a surfactant in an amount of about 25%, sodium carbonate in an amount of about 45%, and cream of tartar in an amount of about 28%.

12. A surfactant product according to claim 1, further comprising one or more cosmetically acceptable additives selected from the group consisting of essential oils, vegetable, vitamins, fragrances, colourings, decorative articles and mixtures thereof.

13. A surfactant product according to claim 12, wherein the decorative articles are selected from the group consisting of flowers, fruits, vegetable, parts thereof and mixtures thereof.

14. A surfactant product according to claim 1, further comprising one or more cosmetically acceptable additives in an amount of from about 0.2% to about 3% by weight of the total composition.

15. A surfactant product according to claim 1, wherein the surfactant product is a bubble bath.

16. A surfactant product according to claim 1, wherein the surfactant product is a shampoo.

17. A surfactant product according to claim 1, wherein the surfactant product is a shower gel.

18. A surfactant product according to claim 1, wherein the surfactant product is a toothpaste.

19. A surfactant product according to claim 1, wherein the surfactant product is a facial wash.

20. A process for the production of a surfactant product as defined in claim 1 comprising the steps of:
   i) preparing a mixture comprising a surfactant, sodium carbonate and cream of tartar;
   ii) allowing the mixture of step i) to solidify.

21. A process according to claim 20, wherein the mixture of step i) is caused to solidify in a predetermined shape.

22. A process according to claim 20, further comprising the step of combining with the mixture of step i) one or more cosmetically acceptable additives selected from the group consisting of essential oils, vegetable, vitamins, fragrances, colourings, decorative articles and mixtures thereof.

23. A product obtained or obtainable by the process of any one of claim 20.

24. A cosmetic method comprising contacting moist skin of a user with the surfactant product as defined in claim 1.

* * * * *